United States Patent [19]

Okabe et al.

[11] Patent Number: 5,744,162
[45] Date of Patent: Apr. 28, 1998

[54] TRANSDERMAL THERAPEUTIC FORMULATION AND A METHOD OF ADMINISTRATION THEREOF

[75] Inventors: Hideaki Okabe, Urawa; Ichiro Tsuchida, Koshigaya; Takanori Saito, Misato, all of Japan

[73] Assignee: Lintec Corporation, Tokyo, Japan

[21] Appl. No.: 929,044

[22] Filed: Aug. 13, 1992

[51] Int. Cl.$^6$ .................................. A61K 9/14
[52] U.S. Cl. .................. 424/486; 424/448; 424/449; 523/111; 602/52; 602/54
[58] Field of Search .................. 424/449, 448, 424/486; 523/111; 602/52, 54

[56] References Cited

U.S. PATENT DOCUMENTS

| | | | |
|---|---|---|---|
| 4,291,015 | 9/1981 | Keith et al. | 424/48 |
| 4,482,534 | 11/1984 | Blank | 424/449 |
| 4,789,547 | 12/1988 | Song et al. | 424/449 |
| 4,914,140 | 4/1990 | Saitoh | 523/111 |
| 5,133,970 | 7/1992 | Petereit | 424/449 |
| 5,186,938 | 2/1993 | Sablotsky | 424/449 |

FOREIGN PATENT DOCUMENTS 0 062 682   10/1982   European Pat. Off.

*Primary Examiner*—D. Gabrielle Phelan
*Attorney, Agent, or Firm*—Millen, White, Zelano, & Branigan, P.C.

[57] ABSTRACT

A transdermal therapeutic formulation is made of a composition comprising a polymer and ingredients mixed with the polymer which are a pharmacologically active substance, an alcohol, a percutaneous absorption promoter utilized according to necessity and water utilized according to necessity. The polymer comprises lipophilic monomer units and hydrophilic monomer units in a specific ratio. The alcohol, the percutaneous absorption promoter and water are mixed with the polymer in specific amounts. The transdermal therapeutic formulation has excellent percutaneous absorption, has many kinds of applicable pharmacologically active substances, shows good stability of percutaneous absorption with time because of absence of crystallization of the pharmacologically active substance, has good adhesive strength and thus favorably utilized as transdermal therapeutic plaster.

22 Claims, No Drawings

TRANSDERMAL THERAPEUTIC FORMULATION AND A METHOD OF ADMINISTRATION THEREOF

BACKGROUND OF THE INVENTION

1. Field of the Invention

The present invention relates to a novel transdermal therapeutic formulation and a method of administration thereof. More particularly, the present invention relates to a transdermal therapeutic formulation having excellent percutaneous absorption of pharmacologically active substances, capable of delivering a desired pharmacologically active substance rapidly to the location of treatment or to all parts of the body through the circulating system, effective for curing various diseases and favorably utilized as a transdermal therapeutic plaster. The present invention relates also to a novel method of administration of the transdermal therapeutic formulation.

2. Description of the Prior Art

During the recent progress of medical treatment, transdermal therapeutic formulations have been developed to absorb percutaneously and deliver desired pharmacologically active substances to all parts of the body and thus to maintain the curing effect for a prolonged time. For example, transdermal therapeutic formulations containing nitroglycerol or isosorbide dinitrate for curing angina pectoris, those containing clonidine for curing hypertonia and those containing estradiol for curing climacteric difficulties have actually been utilized.

However, even though these transdermal therapeutic formulations show many advantages such as evasion of metabolism of the pharmacologically active substances in the intestine and liver, reduction of side reaction and increased retention of the pharmacological effect, they have a problem that, because skin essentially has the barrier function against invasion of foreign substances, only limited kinds of pharmacologically active substances can attain the concentration of the substances in blood high enough to show the pharmacological effect and the pharmacologically active substances which can be utilized for the formulations are naturally very limited.

Various methods have been tried to improve the percutaneous absorption of pharmacologically active substances. For example, pharmacologically active substances were modified to form prodrugs and complexes. Ionic pharmacologically active substances were utilized with use of iontophoresis. These methods have a problem that the actual administration requires detailed studies on the individual pharmacologically active substance and a long period of time and a large amount of investment are inevitably required. On the other hand, percutaneous absorption promoters which increase percutaneous absorption of pharmacologically active substances by decreasing the barrier property of skin have been actively developed. Absorption promoters so far developed have problems that they do not always satisfy both of the promotion of the percutaneous absorption and safety and that a long time is required for exhibition of the pharmacological activity because of a long lag time in the percutaneous absorption of the pharmacologically active substances.

As the form of application of the transdermal therapeutic formulation, plaster, ointment, cream, gel, lotion, liquid and spray have been known and plaster is most widely used among them because of easiness of application and good retention of the pharmacological activity. The plaster of the transdermal therapeutic formulation has a structure comprising a soft supporter and an adhesive layer in which the pharmacologically active substance is dissolved or dispersed. The plaster has problems that percutaneous absorption of the pharmacologically active substance is low and that the kind of the applicable pharmacological substance is limited.

Various trials have been made to solve the problems described above. For example, plasters having increased percutaneous absorption by increasing the concentration of the pharmacologically active substance in the plasters were disclosed in Laid Open Japanese Patent Applications Showa 60-185713 and Showa 63-93714. However, the disclosed plasters have problems that the improvement of the percutaneous absorption is not sufficient and that some of the pharmacologically active substances may sometimes show change of the percutaneous absorption with time caused by crystallization.

SUMMARY OF THE INVENTION

The present invention accordingly has an object to provide a transdermal therapeutic formulation which can solve the problems of conventional transdermal therapeutic formulations, has improved percutaneous absorption, has more kinds of applicable pharmacologically active substances, does not show change of the percutaneous absorption with time and is favorably utilized as a transdermal therapeutic plaster.

Extensive investigations undertaken by the present inventors with an object to develop the transdermal therapeutic formulation having the favorable properties described above led to a discovery that the object can be achieved by a transdermal therapeutic formulation made of a composition comprising a specific polymer and ingredients mixed with the polymer which are a pharmacologically active substance, a specific amount of an alcohol, a specific amount of a percutaneous absorption promoter utilized according to necessity and a specific amount of water utilized according to necessity. The present invention was completed on the basis of this discovery.

Thus, the transdermal therapeutic formulation has adhesive strength of at least 25 g/12 mm and is made of a composition comprising a polymer and ingredients mixed with the polymer, the polymer comprising lipophilic monomer units and hydrophilic monomer units in a weight ratio in the range from 98:2 to 0:100 and the ingredients comprising a pharmacologically active substance, 5 to 100 weight parts of an alcohol, 0 to 50 weight parts of a percutaneous absorption promoter and 0 to 50 weight parts of water, respectively based on 100 weight parts of the polymer.

In the method of administration of a transdermal therapeutic formulation, a patient is applied locally and percutaneously with the transdermal therapeutic formulation which has adhesive strength of at least 25 g/12 mm and is made of a composition comprising a polymer and ingredients mixed with the polymer, the polymer comprising lipophilic monomer units and hydrophilic monomer units in a weight ratio in the range from 98:2 to 0:100 and the ingredients comprising a pharmacologically active substance, 5 to 100 weight parts of an alcohol, 0 to 50 weight parts of a percutaneous absorption promoter and 0 to 50 weight parts of water, respectively based on 100 weight parts of the polymer.

DETAILED DESCRIPTION OF THE INVENTION

In the transdermal therapeutic formulation of the invention, a polymer comprising lipophilic monomer units and hydrophilic monomer units in a specific ratio is utilized as the polymer base material.

Preferable examples of the lipophilic monomer from which the lipophilic monomer units are derived are acrylic ester monomers, such as esters of acrylic acid or methacrylic acid with an alcohol having 1 to 14 carbon atoms, like methanol, ethanol, n-propanol, isopropanol, n-butanol, isobutanol, n-pentanol, 2-pentanol, 3-pentanol, 2-methyl-1-butanol, 3-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-ethylhexanol, n-decanol, lauryl alcohol and the like. The lipophilic monomer may be utilized singly or as a combination of two or more kinds.

Examples of the hydrophilic monomer from which the hydrophilic monomer units are derived are: (meth)acrylic acid, itaconic acid, maleic acid, 2-hydroxyethyl (meth) acrylate, 2-hydroxypropyl (meth)acrylate, 3-hydroxypropyl (meth)acrylate, diethylene glycol (meth)acrylates, triethylene glycol (meth)acrylates, polyethylene glycol (meth) acrylates, dipropylene glycol (meth)acrylates, tripropylene glycol (meth)acrylates, polypropylene glycol (meth) acrylates, trimethylolpropane (meth)acrylates, tetramethylolmethane (meth)acrylates, pentaerythritol (meth)acrylates, glycerol (meth)acrylates, (meth)acrylamide, N,N-dimethylacrylamide, N-vinylpyrrolidone, vinyl ethers and the like. Preferable examples of the hydrophilic monomer are compounds having the formula:

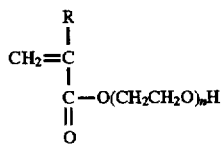

wherein R is a hydrogen atom or methyl group and n is an integer of 1 to 5, such as 2-hydroxyethyl (meth)acrylate, diethylene glycol (meth)acrylates, triethylene glycol (meth) acrylates and the like. The hydrophilic monomer may be utilized singly or as a combination of two or more kinds.

The weight ratio of the content of the lipophilic monomer unit and the content of the hydrophilic monomer unit is selected in the range from 98:2 to 0:100. When the content of the hydrophilic monomer unit is less than the specified range, the percutaneous absorption is not sufficiently enhanced. The weight ratio is selected preferably in the range from 90:10 to 20:80, more preferably in the range from 80:20 to 60:40. When a homopolymer of the hydrophilic monomer is utilized as the polymer in the formulation, the object of the invention can be sufficiently achieved by using, for example, a polyvinyl ether having a low glass transition temperature.

In the preparation of the polymer, a crosslinking monomer is generally utilized in combination with the lipophilic monomer and the hydrophilic monomer. As the crosslinking monomer, compounds having at least two polymerizable double bonds can be utilized. Examples of the crosslinking monomer are: ethylene glycol di(meth)acrylate, propylene glycol di(meth)acrylate, trimethylolpropane tri(meth) acrylate, polyethyleneglycol di(meth)acrylate, polypropylene glycol di(meth)acrylate, tetramethylolmethane tetra (meth)acrylate, pentaerythritol tri(meth)acrylate, glycerol di(meth)acrylate, dipentaerythritol hexa(meth)acrylate, divinylbenzene and the like. The crosslinking monomer is generally utilized in an amount in the range from 0.01 to 1 mol % per total of the lipophilic monomer and the hydrophilic monomer.

The method of preparation of the polymer is not particularly limited but conventional methods utilized for preparation of acrylic resins may be adopted. Examples of such conventional methods are: the method of mixing of a photopolymerization initiator, such as benzyl dimethyl ketal, to a mixture of the lipophilic monomer, the hydrophilic monomer and the crosslinking monomer in a specified ratio, followed by photopolymerization of the mixture by irradiation with an ultraviolet ray; the method of addition of a radical polymerization initiator, such as azo-bis-isobutyronitrile, to a mixture of the lipophilic monomer, the hydrophilic monomer and the crosslinking monomer in a specified ratio, followed by polymerization of the mixture by heating; the method of addition of a crosslinking agent, such as polyfunctional isocyanate, an epoxy resin, a metal chelate compound and the like, to a solution of non-crosslinked polymer of the lipophilic monomer and the hydrophilic monomer in a solvent, followed by heating of the mixture; and other like methods.

The kind of the pharmocologically active substance which is mixed in the polymer is not particularly limited but a suitable substance can be selected and utilized from the generally known pharmacologically active substances. Examples of the pharmacologically active substances are: steroid anti-inflammatory drugs, such as prednisolone, dexamethasone, hydrocortisone, fluocinolone acetonide, betamethasone varelate; betamethasone dipropionate and the like; non-steroid anti-inflammatory drugs, such as indomethacin, diclofenac, ibufenac, ibuprofen, ketoprofen, flufenamic acid, mefenamic acid, phenylbutazone, methyl salicylate and the like; antihistamic drugs, such as diphenhydramine, chlorpheniramine, promethazine, tripelenamine and the like; central nervous system acting drugs, such as chlorpromazine, nitrazepam, diazepam, phenobarbital, reserpine and the like; hormones, such as insulin, testosterone, methyltestosterone, progesterone, estradiol and the like; antihypertensive drugs, such as clonidine, reserpine, guanethidine sulfate and the like; cardiotonics, such as digitoxin, digoxine and the like; antiarrhythmic drugs, such as propranolol hydrochloride, procainamide hydrochloride, ajmaline, pindolol and the like; coronary vaso dilators, such as nitroglycerin, isosorbide dinitrate, erythritose tetranitrate, papaverine hydrochloride, nifedipine and the like; local anesthetics, such as lidocaine, benzocaine, procaine hydrochloride and the like; hypnotics and sedatives, such as barbital, thiopental, phenobarbital, cyclobarbital and the like; analgesics, such as morphine, aspirin, codeine, acetanilide, aminopyrine and the like; antibiotics, such as pencillin, tetracycline, erythromycin, streptomycin, gentamicin and the like; fungicides, such as benzalkonium chloride, acetophenylamine, nitrofurazone, pentamycin, naphthiomate and the like; anticancer drugs, such as 5-fluorouracil, busulfan, actinomycin, bleomycin, mitomycin and the like; diuretics, such as hydrochlorothiazide, penflutide, reserpine and the like; parasympatholytic drugs, such as scopolamine, atropine and the like; antiepileptics, such as nitrazepam, meprobamate and the like; antiparkinsonism drugs, such as chlorzoxazone, levodopa and the like; sulfa drugs, such as sulfamine, sulfamonomethoxine, sulfamethizole and the like; vitamins; prostaglandins; antispasm drugs; contraceptives and the like. The pharmacologically active substances of the invention are, of course, not limited to these examples. The pharmacologically active substance may be utilized singly or as a combination of two or more kinds.

The content of the pharmacologically active substance in the formulation is not particularly limited but suitably selected according to the function of the pharmacologically active substance. The content of the pharmacologically active substance is generally in the range from 1 to 30 weight parts based on 100 weight parts of the polymer.

It is essential in the invention that the alcohol is mixed with the polymer together with the pharmacologically active substance. Examples of the alcohol are: ethyl alcohol, n-propyl alcohol, isopropyl alcohol, ethylene glycol, propylene glycol and the like. Preferable examples among them are ethyl alcohol and propylene glycol. The alcohol may be utilized singly or as a combination of two or more kinds.

The alcohol may also be utilized in combination with water. The amount of the alcohol utilized in the formulation is in the range from 5 to 100 weight parts, preferably in the range from 10 to 80 weight parts, based on 100 weight parts of the polymer. The amount of water utilized in the formulation is in the range from 0 to 50 weight parts, preferably in the range from 10 to 40 weight parts, based on 100 weight parts of the polymer.

In the invention, a percutaneous absorption promoter may be mixed with the polymer according to necessity along with the pharmacologically active substance, the alcohol and water which is also utilized according to necessity. The kind of the percutaneous absorption promoter is not particularly limited but conventional percutaneous absorption promoters may be be utilized. Examples of the percutaneous absorption promoter are: polar solvents, such as dimethylsulfoxide, decylmethylsulfoxide, dimethylformamide, dimethylacetamide and the like; cycloalkanes, such as azacycloheptane-2-one and the like; ester of alcohols and carboxylic acids, such as isopropyl myristate, isopropyl palmitate, diethyl sebacate and the like; glycols; surface active agents, such as sodium laurylsulfate and the like; oils and fats, such as olive oil, squalene, lanolin and the like; fatty acids, pyroglutamic acid and urea derivatives which are natural moisturizing elements of skin; mono and diethanolamides of fatty acids; D-limonene; L-limonene and the like. The preferable example among these compounds is D-limonene.

The percutaneous absorption promoter may be utilized singly or as a combination of two or more kinds. The amount of the percutaneous absorption promoter utilized in the formulation is in the range from 0 to 50 weight parts, preferably in the range from 2 to 40 weight parts based on 100 weight parts of the polymer.

The transdermal therapeutic formulation of the invention is made of the composition comprising the specific polymer and the ingredients mixed with the polymer which are the pharmacologically active substance, the alcohol, the percutaneous absorption promoter utilized according to necessity and water utilized according to necessity. The method of preparation of the composition is not particularly limited. For example, the composition can be prepared by dipping the polymer in a solution containing the desired pharmacologically active substance, the alcohol, the percutaneous absorption promoter utilized according to necessity and water utilized according to necessity in specific amounts and having the the polymer impregnated with the solution. As another example of the preparation of the composition, a solution containing the non-crosslinked polymer, the crosslinking agent, the desired pharmacologically active substance, the alcohol, the percutaneous absorption promoter utilized according to necessity and water utilized according to necessity in specific amounts is cast to form a sheet and then the sheet is heated.

In the composition, various kinds of pharmacologically permissible additives, such as stabilizers, aging preventing agents, antioxidants, perfumes, fillers and the like, may be mixed so long as they do not harm the object of the invention.

The transdermal therapeutic formulation of the invention made of the composition thus prepared show excellent percutaneous absorption of the pharmacologically active substance and no change of the percutaneous absorption with time because the pharmacologically active substance does not crystallize. Furthermore, the formulation has excellent adhesive strength as high as 25 g/12 mm which is measured according to the method of adhesion test of an adhesive plaster described in the dispensatory of the Pharmacopoeia Japonica. Preferable adhesive strength of the transdermal therapeutic formulation of the invention is in the range from 25 to 500 g/12 mm.

The transdermal therapeutic formulation of the invention can be favorably utilized in the form of transdermal therapeutic plasters and the like. The transdermal therapeutic plaster can be prepared, for example, by coating a suitable substrate with a layer of the composition described above to the thickness of about 10~1000 μm, preferably about 20~100 μm, followed by application of a release film treated with a silicone resin or the like to the surface of the layer of the composition. Examples of the substrate utilized herein are: sheet and film of a synthetic resin, such as polyester, polyvinyl chloride, polypropylene, polyethylene, polyurethane and the like; synthetic paper; sheet and film of cellulose based materials; and non-woven fabrics, woven fabrics and knit fabrics of various materials.

The administration of the transdermal therapeutic formulation of the invention to a patient can be made by pasting the formulation to the local portion of the skin of the patient.

DESCRIPTION OF THE PREFERRED EMBODIMENTS

The invention will be understood more readily with reference to the following examples; however, these examples are intended to illustrate the invention and are not to be construed to limit the scope of the invention.

Properties of the transdermal therapeutic formulation were evaluated according to the following methods.

(1) Adhesive strength

Adhesive strength was evaluated according to the method of adhesion test of an adhesive plaster described in the dispensatory of the Pharmacopoeia Japonica.

A test piece having width of 12 mm and length of 250 mm was cut out from a tape plaster and the release film was removed. A test plate of phenolic resin having width of about 25 mm, length of about 125 mm and thickness of about 5 mm was conditioned in advance by standing in a thermostatted chamber at 37° C. for 30 minutes. The test piece was quickly pasted to the test plate so that an end of the test piece was placed to an end of the test plate. Immediately after pasting the test piece, a rubber roller having weight of 850 g was passed over the test piece twice at the speed of 300 mm per minute. After the test piece was left standing in a thermostatted chamber at 37° C. for 30 minutes, the free end of the test piece pasted to the test plate was folded to the angle of 180° and peeled by the length of 25 mm from the end of the test plate. The test piece thus prepared was loaded to a tensile tester by lightly cramping the free end of the test piece and the test plate by the upper cramp and the lower cramp, respectively. The test piece was peeled continuously at the speed of 300 mm per minute. The load of peeling was measured four times at the interval of 20 mm and the results were averaged.

(2) Percutaneous absorption

A test piece of 3.14 cm$^2$ was cut out from a tape plaster and the release film was removed. Hairs of abdominal area of a male Wister rat having a weight of 180 to 200 g were removed by using an animal clipper and the test piece was attached to the skin. After 2, 4, 6 and 8 hours, a sample of blood of 0.3 ml every time was taken from jugular vein and the concentration of the pharmacologically active substance in the blood was quantitatively determined by high speed liquid chromatography to evaluate the percutaneous absorption.

EXAMPLE 1

To a mixture of 60 weight parts of 2-ethylhexyl acrylate and 40 weight parts of acrylic acid, 0.1 mol % of trimethylpropane triacrylate and 1 mol % of benzyl methyl ketal as the photopolymerization initiator were mixed. After oxygen dissolved in the mixture was replaced with nitrogen, the mixture was poured into a vessel of 1 mm depth and irradiated with ultraviolet ray in the nitrogen atmosphere to obtain the crosslinked polymer.

The polymer was purified by removing the monomer remaining in the polymer by extraction with methanol and chloroform successively and dried in vacuo.

The polymer prepared above was dipped into a solution containing 10 weight parts of ketoprofen as the model pharmacologically active substance, 60 weight parts of ethanol and 30 weight parts of water and a transdermal therapeutic formulation containing 40 weight parts of water-ethanol solution of the pharmacologically active substance was prepared.

A layer of the transdermal therapeutic formulation having thickness of 50 µm was formed on a polyester film having thickness of 25 µm and a tape plaster was prepared by pasting to it a release polyester film having thickness of 38 µm which had one of the surfaces treated with a silicone resin in advance. Adhesive strength and percutaneous absorption of the tape plaster thus prepared were evaluated.

EXAMPLE 2

A tape plaster was prepared and the properties of the tape plaster were evaluated by the same method as in Example 1 except that 2-hydroxyethyl acrylate was used in place of acrylic acid in Example 1.

EXAMPLE 3

A tape plaster was prepared and the properties of the tape plaster were evaluated by the same method as in Example 1 except that N-vinyl pyrrolidone was used in place of acrylic acid in Example 1.

EXAMPLE 4

A tape plaster was prepared and the properties of the tape plaster were evaluated by the same method as in Example 1 except that diethylene glycol methacrylate was used in place of acrylic acid in Example 1.

EXAMPLE 5

A tape plaster was prepared and the properties of the tape plaster were evaluated by the same method as in Example 1 except that N,N-dimethylacrylamide was used in place of acrylic acid in Example 1.

EXAMPLE 6

A tape plaster was prepared and the properties of the tape plaster were evaluated by the same method as in Example 1 except that ethyl acrylate was used in place of 2-ethylhexyl acrylate in Example 1 and that diethylene glycol methacrylate was used in place of acrylic acid in Example 1.

EXAMPLE 7

A tape plaster was prepared and the properties of the tape plaster were evaluated by the same method as in Example 6 except that butyl acrylate was used in place of ethyl acrylate in Example 6.

EXAMPLE 8

A tape plaster was prepared and the properties of the tape plaster were evaluated by the same method as in Example 6 except that lauryl acrylate was used in place of ethyl acrylate in Example 6.

EXAMPLE 9

A tape plaster was prepared and the properties of the tape plaster were evaluated by the same method as in Example 6 except that 30 weight parts of ethyl acrylate and 30 weight parts of lauryl acrylate were used in place of 60 weight parts of ethyl acrylate in Example 6.

EXAMPLE 10 TO 18

A tape plaster was prepared and the properties of the tape plaster were evaluated by the same method as in each of Example 1 to 9 except that 4 weight parts of D-limonene were further added to the respective formulation in each of Example 1 to 9.

EXAMPLE 19

A tape plaster was prepared and the properties of the tape plaster were evaluated by the same method as in Example 1 except that 90 weight parts of ethanol alone were used in place of 60 weight parts of ethanol and 30 weight parts of water in Example 1.

COMPARATIVE EXAMPLE 1

The transdermal therapeutic formulation prepared in Example 1 was dried at 100° C. for 3 minutes and then dried in vacuo for one day and one night to remove water and ethanol. Thus, a formulation containing ketoprofen alone was prepared. A tape plaster was prepared by using this formulation and the properties were evaluated by the same method as in Example 1.

COMPARATIVE EXAMPLE 2

An ethyl acetate solution containing 40 weight % of a copolymer prepared by using 40 weight parts of 2-ethylhexyl acrylate, 55 weight parts of butyl acrylate and 5 weight parts of acrylic acid was prepared. To the solution, 4 weight parts of ketoprofen as the model pharmacologically active substance per 100 weight parts of the solid copolymer prepared above were added and the mixture was stirred.

The mixture prepared above was coated on a polyester film having thickness of 25 µm in an amount to form a layer of dried thickness of 50 µm. After the coated film was dried at 90° C. for 3 minutes and then the remaining solvent was removed in vacuo, a tape plaster was prepared by pasting to it a release polyester film having the thickness of 38 µm in which one of the surfaces was treated with a silicone resin in advance. Properties of the tape plaster thus prepared were evaluated.

COMPARATIVE EXAMPLE 3

A tape plaster was prepared and the properties of the tape plaster were evaluated by the same method as in Example 1 except that 110 weight parts of ethanol alone were used in place of 60 weight parts of ethanol and 30 weight parts of water in Example 1.

Results of the evaluation are shown in Table 1.

TABLE 1

|  | adhesive strength (g/12 mm) | concentration in blood (ng/ml) | | | |
|---|---|---|---|---|---|
|  |  | 2 hr | 4 hr | 6 hr | 8 hr |
| Example 1 | 130 | 630 | 770 | 780 | 870 |
| Example 2 | 125 | 540 | 330 | 770 | 1010 |
| Example 3 | 215 | 300 | 430 | 290 | 280 |
| Example 4 | 200 | 710 | 880 | 1050 | 1410 |
| Example 5 | 285 | 520 | 420 | 700 | 660 |
| Example 6 | 75 | 220 | 440 | 340 | 360 |
| Example 7 | 125 | 490 | 810 | 1420 | 1650 |
| Example 8 | 195 | 900 | 1250 | 2310 | 2350 |
| Example 9 | 180 | 1940 | 1890 | 2980 | 3040 |
| Example 10 | 145 | 1430 | 1510 | 2050 | 1950 |
| Example 11 | 140 | 720 | 930 | 950 | 1070 |
| Example 12 | 225 | 1210 | 1260 | 1550 | 2040 |
| Example 13 | 195 | 1310 | 2340 | 2820 | 2790 |
| Example 14 | 275 | 480 | 520 | 740 | 890 |
| Example 15 | 80 | 1850 | 4080 | 4860 | 5340 |
| Example 16 | 140 | 1820 | 2550 | 3300 | 3230 |
| Example 17 | 185 | 2650 | 3840 | 3970 | 4120 |
| Example 18 | 140 | 3430 | 3030 | 4270 | 4360 |
| Example 19 | 45 | 720 | 930 | 950 | 1030 |
| Comparative Example 1 | 315 | 140 | 190 | 170 | 210 |
| Comparative Example 2 | 410 | 200 | 250 | 230 | 240 |
| Comparative Example 3 | 0 | 590 | 320 | 270 | 290 |

As the results in Table 1 show, all of the transdermal therapeutic formulation of the invention had a higher concentration in blood than those of Comparative examples.

The conventional acrylic adhesive became tack-free by the effect of water. On the other hand, the present invention show that compositions having good adhesive property could be prepared by increasing the content of the hydrophilic monomer unit even when water and ethanol were contained.

While the invention has been particularly shown and described with reference to preferred embodiments thereof, it will be understood by those skilled in the art that the foregoing and other changes in form and details can be made therein without departing from the spirit and scope of the invention.

To summarize the advantages obtained by the invention, the transdermal therapeutic formulation has excellent percutaneous absorption, has many kinds of applicable pharmacologically active substances, shows good stability of percutaneous absorption with time because of absence of crystallization of the pharmacologically active substance, has good adhesive strength and is thus favorably utilized as transdermal therapeutic plaster.

What is claimed is:

1. In a transdermal therapeutic adhesive composition comprising an adhesive layer containing a pharmacologically active agent and adapted to adhere the composition to the skin, the improvement wherein the adhesion of the composition to the skin is provided by a polymer having lipophilic monomer units and hydrophilic monomer units in a weight ratio in the range from 98:2 to 0:100, wherein the composition has an adhesive strength of at least 25 g/12 mm and wherein the composition comprises 5 to 100 weight parts of a $C_2$–$C_3$ alcohol, 0 to 50 weight parts of a percutaneous absorption promoter and 10 to 40 weight parts of water, respectively based on 100 weight parts of the polymer.

2. A transdermal therapeutic formulation as claimed in claim 1, wherein the hydrophilic monomer units are derived from a monomer having the formula:

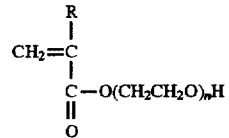

wherein R is a hydrogen atom or a methyl group and n is an integer from 1 to 5.

3. A transdermal therapeutic formulation as claimed in claim 1 wherein lipophilic monomer units are derived from an acrylic ester monomer.

4. A transdermal therapeutic formulation as claimed in claim 1 wherein the weight ratio of the content of the lipophilic monomer units and the content of the hydrophilic monomer units is in the range from 90:10 to 20:80.

5. A transdermal therapeutic formulation as claimed in claim 1 wherein the weight ratio of the content of the lipophilic monomer units and the content of the hydrophilic monomer units is in the range from 80:20 to 60:40.

6. A transdermal therapeutic formulation as claimed in claim 1 wherein the polymer also comprises crosslinking monomer units in the range from 0.01 to 1 mol % based on the total of the lipophilic monomer units and the hydrophilic monomer units.

7. A transdermal therapeutic formulation as claimed in claim 1, which contains an amount of alcohol in the range from 10 to 80 weight parts based on 100 weight parts of the polymer.

8. A transdermal therapeutic formulation as claimed in claim 1 wherein the alcohol is ethyl alcohol or propylene glycol.

9. A tape plaster adapted for application to the skin comprising a backing film having on one face thereof a layer of a transdermal therapeutic formulation as claimed in claim 1 wherein the hydrophilic monomer units are derived from a monomer having the formula:

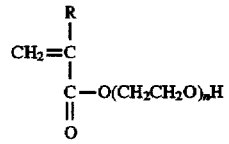

wherein R is a hydrogen atom or a methyl group and n is an integer from 1 to 5; wherein the lipophilic monomer units are derived from an acrylic ester monomer; wherein the weight ratio of the content of the lipophilic monomer units and the content of the hydrophilic monomer units is in the range from 90:10 to 20:80; wherein the polymer also comprises crosslinking monomer units in the range from 0.01 to 1 mol % based on the total of the lipophilic monomer units and the hydrophilic monomer units; and wherein the composition contains from 10 to 80 weight parts of ethyl alcohol or propylene glycol and 10 to 40 weight parts of water, based on 100 weight parts of the polymer.

10. A transdermal therapeutic formulation as claimed in claim 1 containing an amount of percutaneous absorption promoter in the range from 2 to 40 weight parts based on 100 weight parts of the polymer.

11. In a method of administration of a pharmacologically active agent in which a transdermal therapeutic formulation comprising the agent is applied locally and percutaneously to the skin of a patient, the improvement wherein the formulation applied to the skin is a transdermal therapeutic formulation as claimed in claim 1.

12. A method of administration of a transdermal therapeutic formulation as claimed in claim 11 wherein the hydrophilic monomer units are derived from a monomer having the formula:

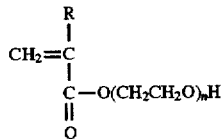

wherein R is a hydrogen atom or a methyl group and n is an integer from 1 to 5.

13. A method of administration of a transdermal therapeutic formulation as claimed in claim 11 wherein the lipophilic monomer units are derived from an acrylic ester monomer.

14. A method of administration of a transdermal therapeutic formulation as claimed in claim 11 wherein the weight ratio of the content of the lipophilic monomer units and the content of the hydrophilic monomer units is in the range from 90:10 to 20:80.

15. A method of administration of a transdermal therapeutic formulation as claimed in claim 11 wherein the weight ratio of the content of the lipophilic monomer units and the content of the hydrophilic monomer units is in the range from 80:20 to 60:40.

16. A method of administration of a transdermal therapeutic formulation as claimed in claim 11 wherein the polymer also comprises crosslinking monomer units in the range from 0.01 to 1 mol % based on the total of the lipophilic monomer units and the hydrophilic monomer units.

17. A method of administration of a transdermal therapeutic formulation as claimed in claim 11 which contains an amount of alcohol in the range from 10 to 80 weight parts based on 100 weight parts of the polymer.

18. A method of administration of a transdermal therapeutic formulation as claimed in claim 11 wherein the alcohol is ethyl alcohol or propylene glycol.

19. A method of administration of a transdermal therapeutic formulation as claimed in claim 11 wherein the hydrophilic monomer units are derived from a monomer having the formula:

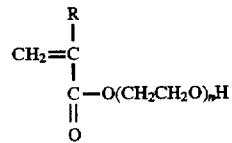

wherein R is a hydrogen atom or a methyl group and n is an integer from 1 to 5; wherein the lipophilic monomer units are derived from an acrylic ester monomer; wherein the weight ratio of the content of the lipophilic monomer units and the content of the hydrophilic monomer units is in the range from 90:10 to 20:80; wherein the polymer also comprises crosslinking monomer units in the range from 0.01 to 1 mol % based on the total of the lipophilic monomer units and the hydrophilic monomer units; and wherein the composition contains from 10 to 80 weight parts of ethyl alcohol or propylene glycol and 10 to 40 weight parts of water, based on 100 weight parts of the polymer.

20. A method of administration of a transdermal therapeutic formulation as claimed in claim 11 containing an amount of percutaneous absorption promoter in the range from 2 to 40 weight parts based on 100 weight parts of the polymer.

21. The tape plaster of claim 9 wherein the weight ratio of the content of the lipophilic monomer units and the content of the hydrophilic monomer units is in the range from 80:20 to 60:40.

22. The method of administration of a transdermal therapeutic formulation of claim 19 wherein the weight ratio of the content of the lipophilic monomer units and the content of the hydrophilic monomer units is in the range from 80:20 to 60:40.

* * * * *